(12) United States Patent
Reichow et al.

(10) Patent No.: US 7,950,803 B2
(45) Date of Patent: May 31, 2011

(54) PERSPECTIVE VISION TUNNEL

(75) Inventors: Alan W. Reichow, Beaverton, OR (US);
Herb Yoo, Beaverton, OR (US); Ryan C. Coulter, Portland, OR (US);
Christian Freissler, Portland, OR (US);
Dave Knaub, Portland, OR (US); Meral Middleton, Portland, OR (US); David Thorpe, Portland, OR (US); Tom Lakovic, Portland, OR (US); Andrew Allen, Seattle, WA (US); Josh Hoyt, Portland, OR (US)

(73) Assignee: Nike, Inc., Beaverton, OR (US)

( * ) Notice: Subject to any disclaimer, the term of this patent is extended or adjusted under 35 U.S.C. 154(b) by 9 days.

(21) Appl. No.: 12/534,558

(22) Filed: Aug. 3, 2009

(65) Prior Publication Data

US 2011/0025980 A1 Feb. 3, 2011

(51) Int. Cl.
*A61B 3/02* (2006.01)
*A61B 3/10* (2006.01)

(52) U.S. Cl. .......................... 351/237; 351/239; 351/211

(58) Field of Classification Search ........... 351/200–246
See application file for complete search history.

(56) References Cited

U.S. PATENT DOCUMENTS

| 6,511,181 | B1 * | 1/2003 | Fujieda ......................... 351/245 |
| 7,441,900 | B2 * | 10/2008 | Mihashi et al. ............... 351/239 |
| 7,802,886 | B2 * | 9/2010 | Kawai ........................... 351/211 |

\* cited by examiner

*Primary Examiner* — Mohammed Hasan
(74) *Attorney, Agent, or Firm* — Shook, Hardy & Bacon L.L.P.

(57) ABSTRACT

Devices and methods for testing a subject's visual ability are provided. More specifically, the device may include a perspective vision tunnel comprised of plurality of low reflectance walls with one or more mirrors arranged within the perspective vision tunnel. Visual indicia for administering the test of a subject's visual ability are displayed into a first portion of the perspective vision tunnel. The one or more mirrors are arranged to reflect the visual indicia out of the first portion such that visual indicia may be visually perceived by the subject. In accordance with the invention, a subject may be tested utilizing the perspective vision tunnel and input may be received from the individual. The received input may then, for example, be used to compute data related to the user's visual ability.

18 Claims, 8 Drawing Sheets

PERSPECTIVE VISION TUNNEL

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention relates generally to the evaluation and/or diagnosis of an individual's visual abilities.

BACKGROUND

In order to accurately evaluate an individual's visual abilities the individual may be required to respond to a variety of visual stimuli located at a distance greater than or equal to optical infinity from the individual. Typically, a large, dedicated space is therefore required to accurately evaluate the visual abilities of an individual. By decreasing the overall size of the area required to evaluate visual ability, the evaluation may be performed in a more efficient and productive manner.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with the invention, a device and method for testing the visual acuity of a subject is provided. A device in accordance with the present invention may include a display tunnel defined by a plurality of low reflectance walls having a first portion extending substantially perpendicularly from a display and at least one mirror arranged within the tunnel to reflect test images output from the display out of the first portion of the tunnel so that the test images are able to be visually perceived by a subject outside of the tunnel. In accordance with the invention, the tunnel may have multiple portions and a plurality of minors arranged therein to reflect the test images within the tunnel before exiting. The minors may be oriented within the perspective vision tunnel in order to generate the perspective that the test images are located at a distance greater that physical distance between the subject and the display. A visual test and/or training may be administered to a subject using the perspective vision tunnel, and the subject may generate input(s) in response to viewing the test images.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

In accordance with the present invention, devices and methods for testing and/or training a subject's visual ability are provided. In one embodiment, a device for administering a visual test to a subject is provided. Such a device, referred to herein as a perspective tunnel, may include a display tunnel to output test images, the display tunnel being defined by a plurality of low reflectance walls and having a first portion extending substantially perpendicularly to a display device. The perspective tunnel may also include at least one minor arranged within the display tunnel and oriented to reflect test images output on the display device out of this first portion of the tunnel such that the test images may be visually perceived by a subject from outside of the tunnel.

In another embodiment, a device for administering a visual test is provided. The device may include a perspective tunnel that transmits visible light along the interior of the perspective tunnel and comprising a first portion, a second portion, and an output portion. The first portion and the second portion may be substantially parallel, and the output portion may provide egress for visible light from the second portion to the exterior of the perspective tunnel. The device may further provide a display to output visual stimuli comprised of visible light into the first portion of the perspective tunnel and a plurality of mirrors oriented within the perspective tunnel to reflect the visible light within the perspective tunnel along the first portion, then the second portion, and then through the output portion to egress the perspective tunnel.

In another embodiment, a method for testing the visual ability of a subject is provided. Such a method may include displaying a visual stimulus on a display component into a perspective tunnel and reflecting the visual stimulus within the perspective tunnel and thereby generating the perspective that that the visual stimulus is located at a greater distance from the subject than the physical distance between the display component and the subject. A visual stimulus may then be presented to a subject positioned on the exterior of the perspective tunnel and input may be received from the subject in response to the visual stimulus.

Figure 1:
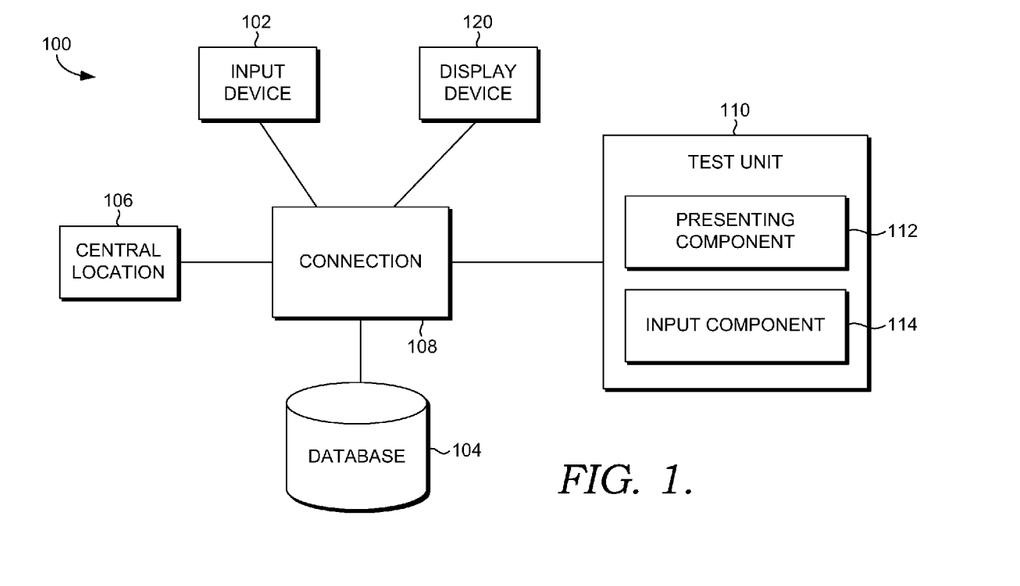
FIG. 1 is a block diagram of a computing system environment suitable for use in implementing the present invention.

The input device 102 is capable of receiving one or more responses from a subject. Input device 102 may be any device that may receive responses from a subject. One skilled in the art will appreciate that more than one input device, such as input device 102, may be used with computing system 100. Input device 102 may be, for example, a microphone, joystick, game pad, wireless device, keyboard, keypad, game controller, treadmill, force plate, and any other input-receiving component that may provide wired or wireless input data to the test unit 110. Input device 102 may include voice recognition equipment and/or software that processes auditory inputs from the test subject. For example, the auditory input from the subject, in order to show recognition of the visual indicia, may be a verbalization of the trait possessed by the visual indicia.

In one embodiment, input device 102 may comprise a joystick, and the trait possessed by a visual indicia may be the directional orientation of a Landolt "C." In this example, inputs may be moving the joystick up, down, right, and/or left. However, other inputs, such as auditory inputs (e.g., stating a color, numeral, letter, symbol, etc.), may be used to indicate that the subject perceived and/or recognized the visual indicia. It should be noted, however, that the present invention is not limited to implementations using a joystick and/or microphone as input device 102, but rather the present invention may be implemented on any of a variety of different types of devices, such as multi-touch devices, buttons, etc., within the scope of embodiments hereof.

The display device 120 may be capable of displaying at least one visual indicia. Display device 120 may be any type of monitor, such as a computer monitor or television monitor, including cathode ray tube, liquid crystal display, plasma screen, or any other display type, or may comprise a screen upon which images are projected, either from the front or from the rear. Display device 120 may display one or more visual indicia. Visual indicia may possess one or more visual characteristic, such as orientation, color, identity (such as of a letter or number, for example), etc. Further, an indicia may be displayed on display device 120 alone or in combination with other indicia. For example, an indicia may be displayed in conjunction with a picture or video (real or simulated) of a objects, locations, activities, etc. Further, the display device 120 may provide a user interface for a test administrator to interact with the test unit 110 before, during, and after administering the vision ability tests to a test subject.

The test unit 110, as shown in FIG. 1, may be any type of computing device, embodiments of which will be more fully discussed below with reference to FIGS. 4 and 5. The database 104 may be configured to store information associated with tests of visual ability. The information stored in the database 104 may be configurable and may include any information relevant to the testing and/or training of visual ability. The content and volume of such information are not intended to limit the scope of embodiments of the present invention in any way. Although illustrated as a single, independent component, database 104 may, in fact, be a plurality of databases, for instance, a database cluster. Further, portions or the entirety of the database 104 may reside on a computing device associated with the test unit 110, another external computing device (not shown), and/or any combination thereof. One skilled in the art should appreciate that database 104 is optional and need not be implemented in conjunction with the computing system 100.

Returning to FIG. 1, the test unit 110 may include a presenting component 112 and an input component 114, shown in accordance with an embodiment of the present invention. Any number of components may be employed to achieve the desired functionality within the scope of embodiments of the present invention. The presenting component 112 may be capable of displaying output video visually observable by a subject on display device 120.

In operation, the presenting component 112 may be configured to control display device 120 to present one or more visual indicia to a test subject. As discussed more fully below, presenting component 112 may present visual indicia in varying ways to test different aspects of the subject's visual ability. In general, each of the visual indicia may possess a trait or traits. This trait may be, for example, a directional orientation (e.g., arrow, Landolt "C", Tumbling E, etc.), color, a position on a user interface (e.g., located in a particular quadrant of the display), one of a predetermined number of mutually exclusive traits (e.g., indicator that faces either up, down, left, or right), an identity (e.g., which letter, which number, what item is pictured, etc.), any other trait, or any combination of traits. Further, one of ordinary skill in the art will understand and appreciate that other traits may be used, and the present invention is not limited to any particular trait.

The input component 114 may be configured to receive input from the test subject from input device 102. Any suitable receiving component that is capable of receiving input provided by the subject may be used in accordance with this invention. For example, if input device 102 comprises a microphone input component 114 could include voice recognition software. One skilled in the art will understand and appreciate that any suitable input component may be used in accordance with the present invention. Certain types may be preferred based, for example, on the indicia displayed on display device 120 and the characteristics displayed indicia possess, such as a joystick or directional keys being used for indicia having directional orientation. After receiving input from the subject, the input component 114 may store the input, for instance, in database 104 for future reference.

Figure 2:
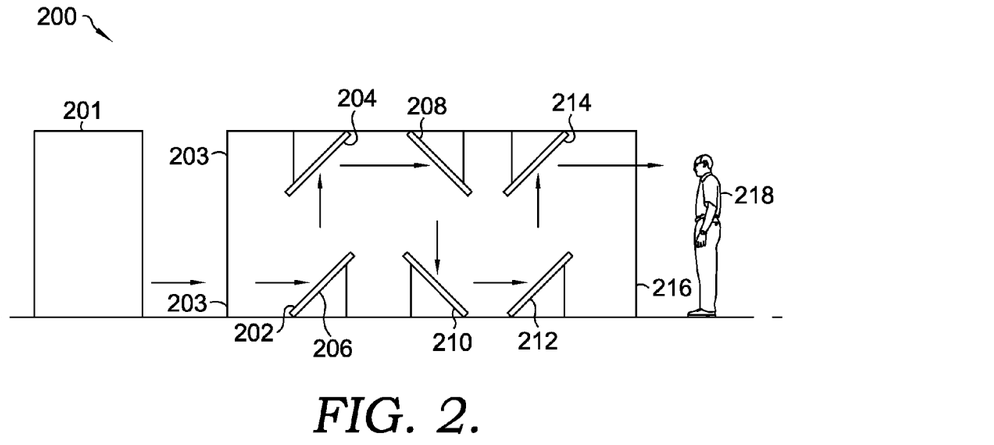
FIG. 2 illustrates an exemplary perspective vision tunnel, in accordance with the present invention.

Referring now to FIG. 2, an exemplary perspective tunnel is further illustrated. The terms "display tunnel," "perspective tunnel," and "vision perspective tunnel" are used interchangeably herein, and should be understood to be synonymous. Perspective tunnel 200 may comprise a plurality of low reflectance walls 202, which serve to form a tunnel and substantially prevent the intrusion of light from outside the perspective tunnel 200. The plurality of low reflectance walls 202 may be substantially parallel and have an opening 203 at one end to permit entry of test images from display device 202 and an opening 216 that permits egress of the test images from the perspective tunnel 200. Additionally, arrows showing the path of the light comprising visual indicia from the display device 202 to the subject 218 have been presented in FIGS. 2-8 for clarity. None of FIGS. 2-8 are necessarily to scale. A perspective tunnel in accordance with the present invention may be of any size relative to the individual using the perspective tunnel for testing and/or training. The arrows serve to show the path that the visual light comprising the visual indicia travels through the perspective tunnel 200.

Display device 202 may be positioned directly within opening 203 of the perspective tunnel 200 such that ambient light may be substantially prevented from entering the tunnel through the opening 203. Additional material may be used around the opening 203 to prevent ambient light from entering tunnel 200 and to account for any difference in overall dimensions between the display unit 201 and the opening 203 of the perspective tunnel. This material may be any material suitable for the purpose, and in some embodiments of the invention may be of the same type as the plurality of low reflectance walls 202.

A plurality of minors 204, 206, 208, 210, 212, and 214 may be positioned within tunnel 200 so as to reflect visual indicia displayed on display device 202 within the perspective tunnel 200. The minors 208, 210, 212, and 214 may be of the simple plane type, or may be any other form of suitable mirror. The mirrors 208, 210, 212, and 214 are oriented so as to reflect the visual indicia from the opening 203 of the perspective tunnel to opening 216 at the opposite end of perspective tunnel 200. By reflecting the visual indicia in a path through perspective tunnel 200, the light comprising visual indicia will travel a greater distance than the direct physical distance between the display component 201 and a subject 218. The actual distance traveled by the light comprising the visual indicia may be adjusted by altering the placement, type, and number of mirrors arranged within the perspective tunnel 200.

The subject 218 may be positioned to view the visual indicia as it egresses from the perspective tunnel through the opening 216. Subject 218 may be positioned directly adjacent to the opening 216 of the perspective tunnel 200 or at a distance from opening 216 of tunnel 200. By positioning subject 216 directly adjacent to opening 216, ambient light may be substantially prevented from entering the perspective tunnel 200 through the opening 216.

Alternative embodiments may utilize additional material around the opening 216 to account for differences in overall dimensions between the opening 216 of the perspective tunnel and the face of subject 218 surrounding their eyes. This additional material may be configured into a shape that substantially conforms to the portion of the face of subject 218. This material may be any material suitable for the purpose, and in some embodiments of the invention may be a substantially opaque, moderately flexible material that easily conforms to the shape of the face of subject 218 so that a plurality of subjects 218 may be accommodated by the additional material.

In some embodiments of the invention, the distance traveled by the light comprising a visual indicia displayed on display device 220 in reaching subject 210 may substantially equal a distance approximating optical infinity. The distance of optical infinity is approximately 20 feet, or 6 meters. At this distance, the eyes of an individual, such as subject 218, must be directed essentially parallel in order to resolve a displayed indicia. By utilizing the plurality of mirrors 204, 206, 208, 210, 212, and 214 to reflect the visual indicia along a circuitous path, the space the perspective tunnel 200 may substantially less than that of optical infinity, thereby significantly reducing the space required for vision testing and/or training using indicia at optical infinity. The perspective tunnel 200 may then be portable in nature. In addition, since the perspective tunnel 200 is formed from a plurality of low reflectance walls 200, the perspective tunnel may be used in environments having high levels of ambient light that might make particular types of low luminescence devices otherwise difficult to use as display device 220. The perspective tunnel may then be used to administer visual ability tests in well light indoor locations, as well as outdoor conditions, even when ambient light conditions are high.

Figure 3:
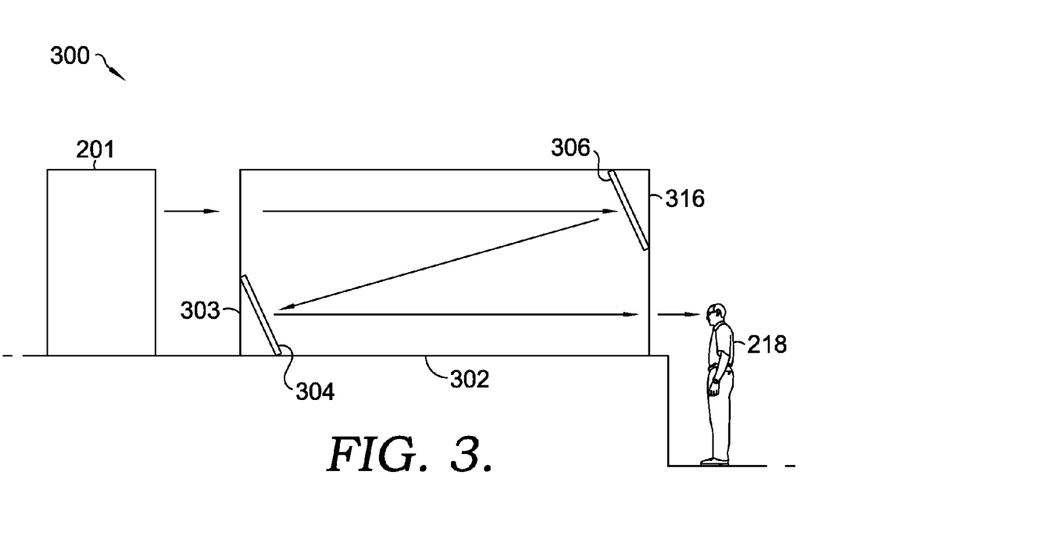
FIG. 3 illustrates a perspective vision tunnel, in accordance with an embodiment of the present invention.

Referring now to FIG. 3, a perspective tunnel according to another embodiment of the invention is provided. FIGS. 3-8 operate under the same principles as FIG. 2, as described above. The perspective tunnel 300 may be comprised of a plurality of low reflectance walls 302 in substantially the same form as depicted in FIG. 3. The position of the display unit 201 and the subject 218 is similar to that of FIG. 2, as described above.

The plurality of mirrors 304 and 306 may be arranged within the perspective tunnel 300 in an arrangement differing from that depicted in FIG. 2. Two mirrors 304 and 306 are shown in FIG. 3, although it should be understood that this depiction is not meant to be limiting. Any number of mirrors may arranged within the perspective tunnel 300 to reflect the visual indicia along the longitudinal axis.

Figure 4:
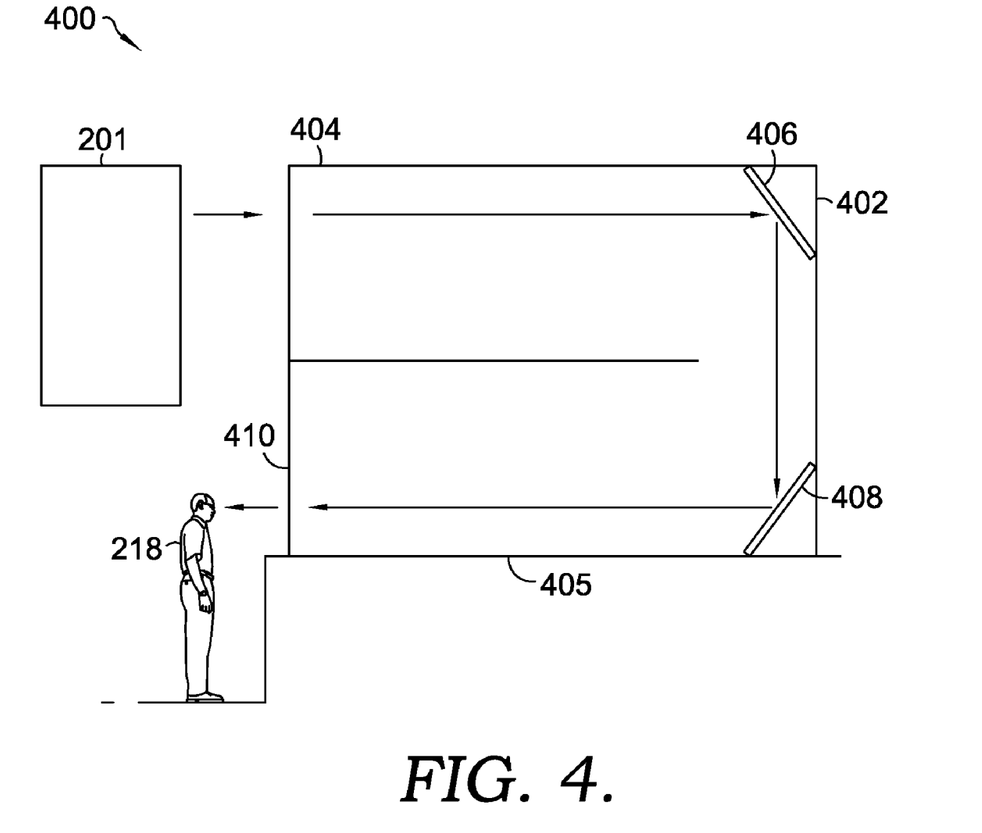
FIG. 4 illustrates another embodiment of a perspective vision tunnel, in accordance with the present invention.

Turning now to FIG. 4, another embodiment of a perspective vision tunnel in accordance with the present invention is illustrated. While composed of a plurality of low reflectance walls 402, the perspective tunnel 400 comprises a first portion 404 and a second portion 405. As depicted in FIG. 4, the longitudinal axis, denoted 414, of the first portion 404 is substantially parallel to the longitudinal axis, denoted 415, of the second portion 405. The plurality of mirrors 406 and 408 are arranged within the tunnel to reflect the image of visual indicia output by display device 201 through first portion 404, through second portion 405, and out through output portion 410 for viewing by the subject 218.

Figure 5:
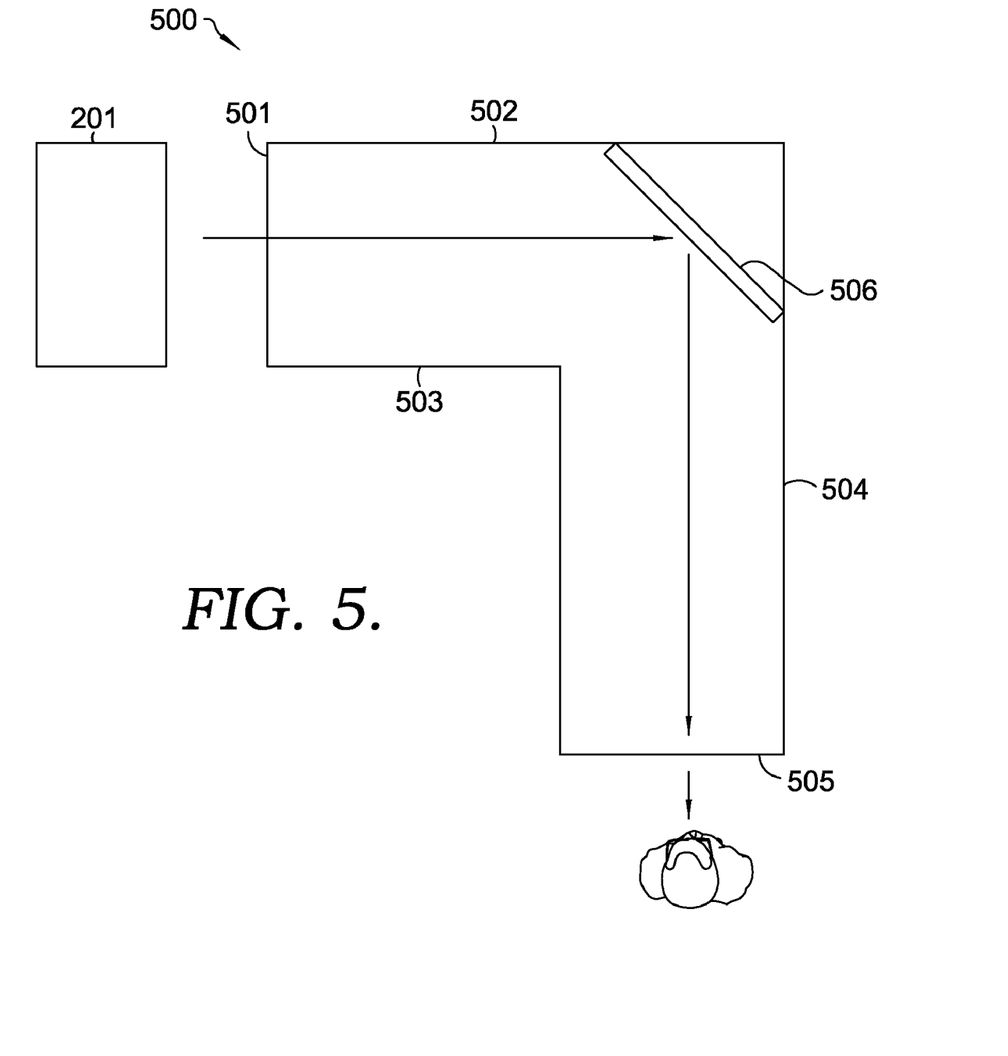
FIG. 5 illustrates a perspective vision tunnel, in accordance with an embodiment of the present invention.

Referring now to FIG. 5, a further embodiment of a perspective vision tunnel in accordance with the present invention is provided. The perspective tunnel 500 comprises a plurality of low reflectance walls 503, such as those discussed in regards to FIGS. 2, 3, and 4, above. Perspective tunnel 500 comprises a first portion 502 and a second portion 504. As shown in FIG. 5, the longitudinal axis, denoted 512, of the first portion 502 is substantially perpendicular to the longitudinal axis, denoted 514, of the second portion 504. A mirror 506 may be positioned to reflect the image of a visual indicia output by display device 201 through the opening 501 of the perspective tunnel 500 into the first portion 502 and then into the second portion 504 before exiting through the opening 505 of the perspective tunnel 500 for viewing by the subject 518.

It should be understood that the arrangements of the first portion 502 and second portion 504 depicted in FIGS. 4 and 5 are intended to be exemplary in nature. The portions of a perspective vision tunnel in accordance with the present invention may be arranged in any number of configurations and/or dimensions, and are not limited to the configurations depicted in FIGS. 4 and 5. For instance, the first and second portions may be arranged such that they lie in intersecting planes. Furthermore, the perspective tunnel 500 may be comprised of additional portions composed of a plurality of low reflectance walls along which the visual is reflected by a plurality of mirrors. Accordingly, a multitude of different configurations may be employed to practice alternative embodiments of the invention.

Figure 6:
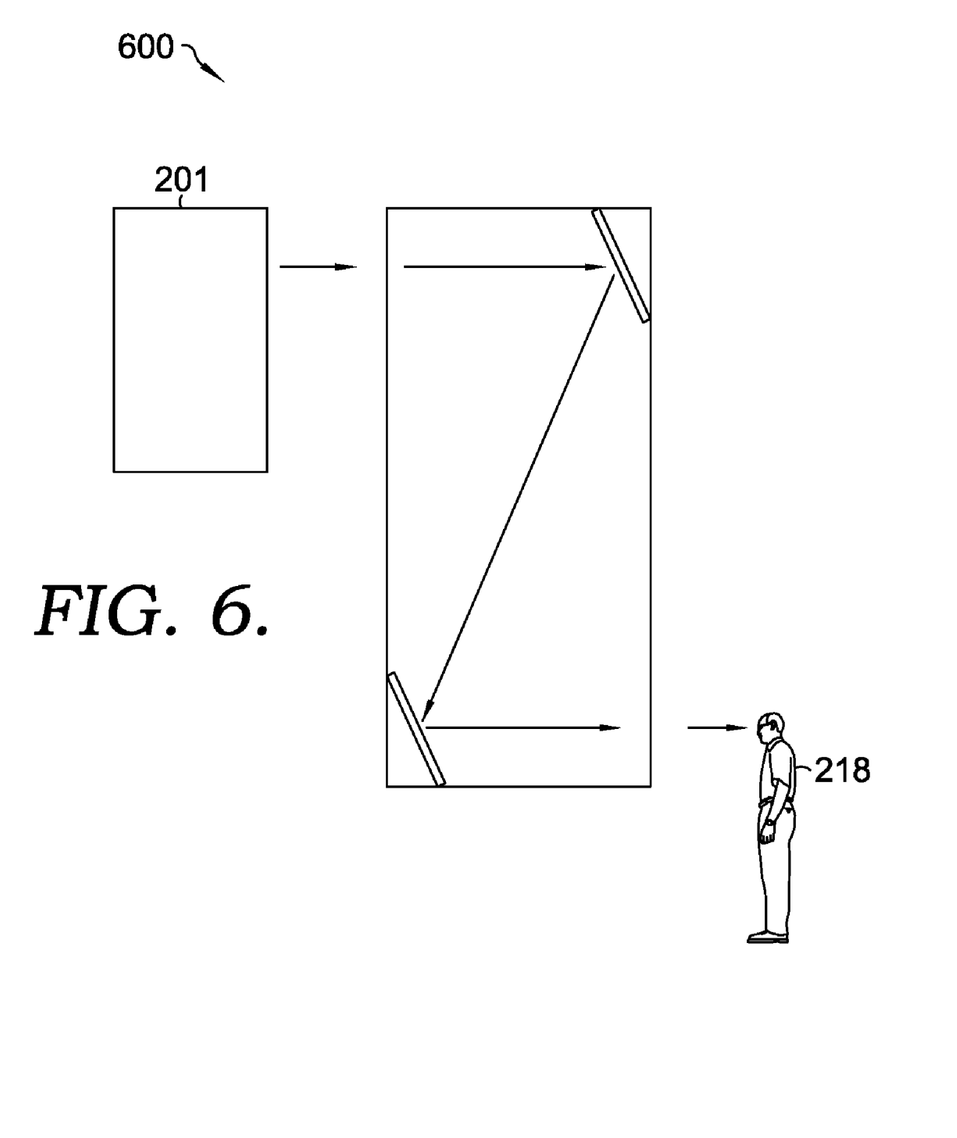
FIG. 6 illustrates another embodiment of a perspective vision tunnel, in accordance with the present invention.

Turning to FIG. 6, yet a further embodiment of a perspective vision tunnel in accordance with the present invention is illustrated. The perspective tunnel 600 is similar in configuration and construction as the perspective tunnel 300 depicted in FIG. 3, discussed above. However, the perspective tunnel 600 is oriented in a vertical fashion in FIG. 6. The display device 601 is positioned atop the perspective tunnel 600, and the subject 618 is positioned at the opposite end of the perspective tunnel 600 from display device 601. A plurality of mirrors 604 and 606 are arranged within the perspective tunnel 600 to reflect the image of a visual indicia output from display device 601 through and out of the perspective tunnel 600 for viewing by the subject 618. The plurality of mirrors 604 and 606 are arranged in FIG. 6 to reflect the image of a visual indicia primarily along the longitudinal axis of the perspective tunnel 600, however the mirrors may also be arranged in alternative configurations that serve to reflect the visual indicia along the lateral axis of the perspective tunnel 600 and/or the longitudinal axis of the perspective tunnel 600.

In addition to vertical orientation of the perspective tunnel 600 depicted in FIG. 6, and the horizontal orientation depicted in FIG. 3, alternative embodiments may utilize any number of orientations and/or dimensions of a perspective tunnel, and are not limited to the orientations and/or dimensions depicted in any of the Figures.

Figure 7:
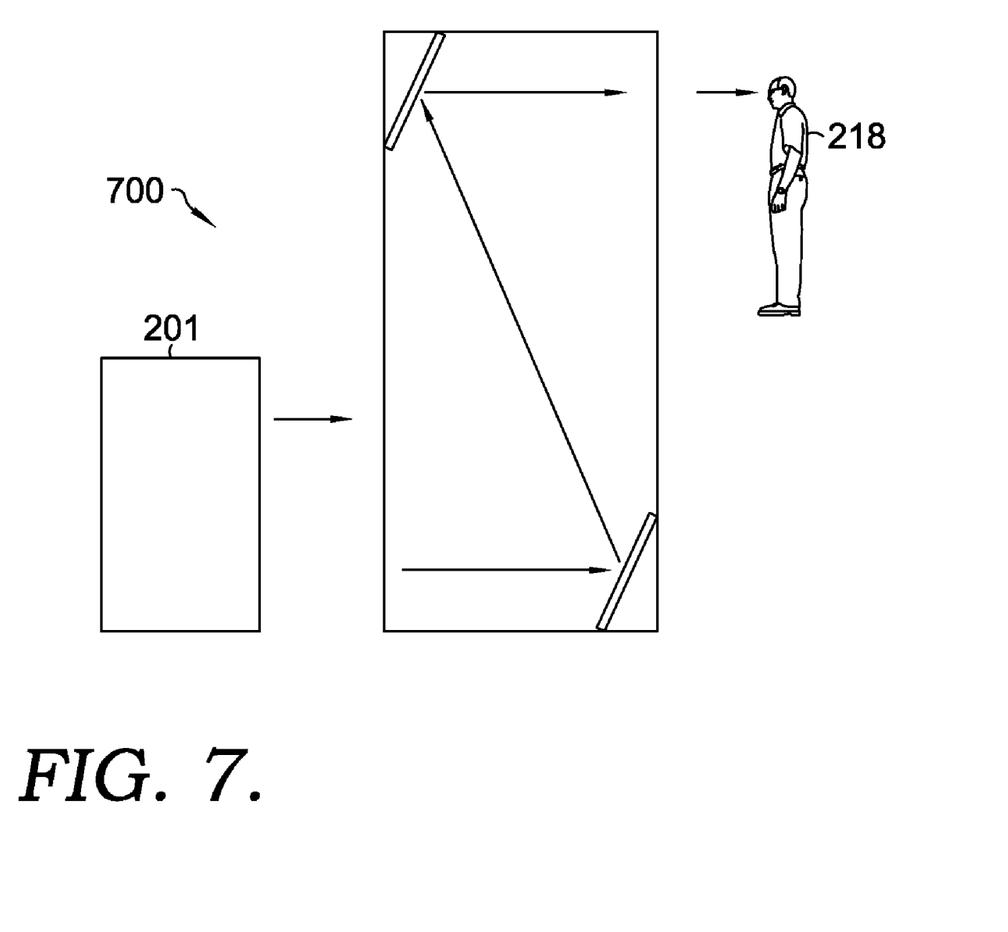
FIG. 7 illustrates a perspective vision tunnel according to an alternative embodiment of the present invention.

Turning now to FIG. 7, a further embodiment of a visual perspective tunnel in accordance with the present invention is illustrated. This embodiment is similar to that depicted in FIG. 6. However, the subject 618 is positioned atop the perspective tunnel 700, with the display unit 701 positioned at the opposite end of the perspective tunnel 700 from subject 718. The perspective tunnel 700 may otherwise be similar in configuration and construction to perspective tunnel 600. A plurality of mirrors 704 and 706 may be arranged within perspective runnel 700 to reflect an image of a visual indicia output by display device 701 through and out of the perspective tunnel 700 for viewing by the subject 718.

The plurality of mirrors 704 and 706 are arranged in FIG. 7 to reflect the visual indicia primarily along the longitudinal axis of the perspective tunnel 700, however the mirrors may also be arranged in alternative configurations that serve to reflect the visual indicia along the lateral axis of the perspective tunnel 700 and/or the longitudinal axis of the perspective tunnel 700.

Figure 8:
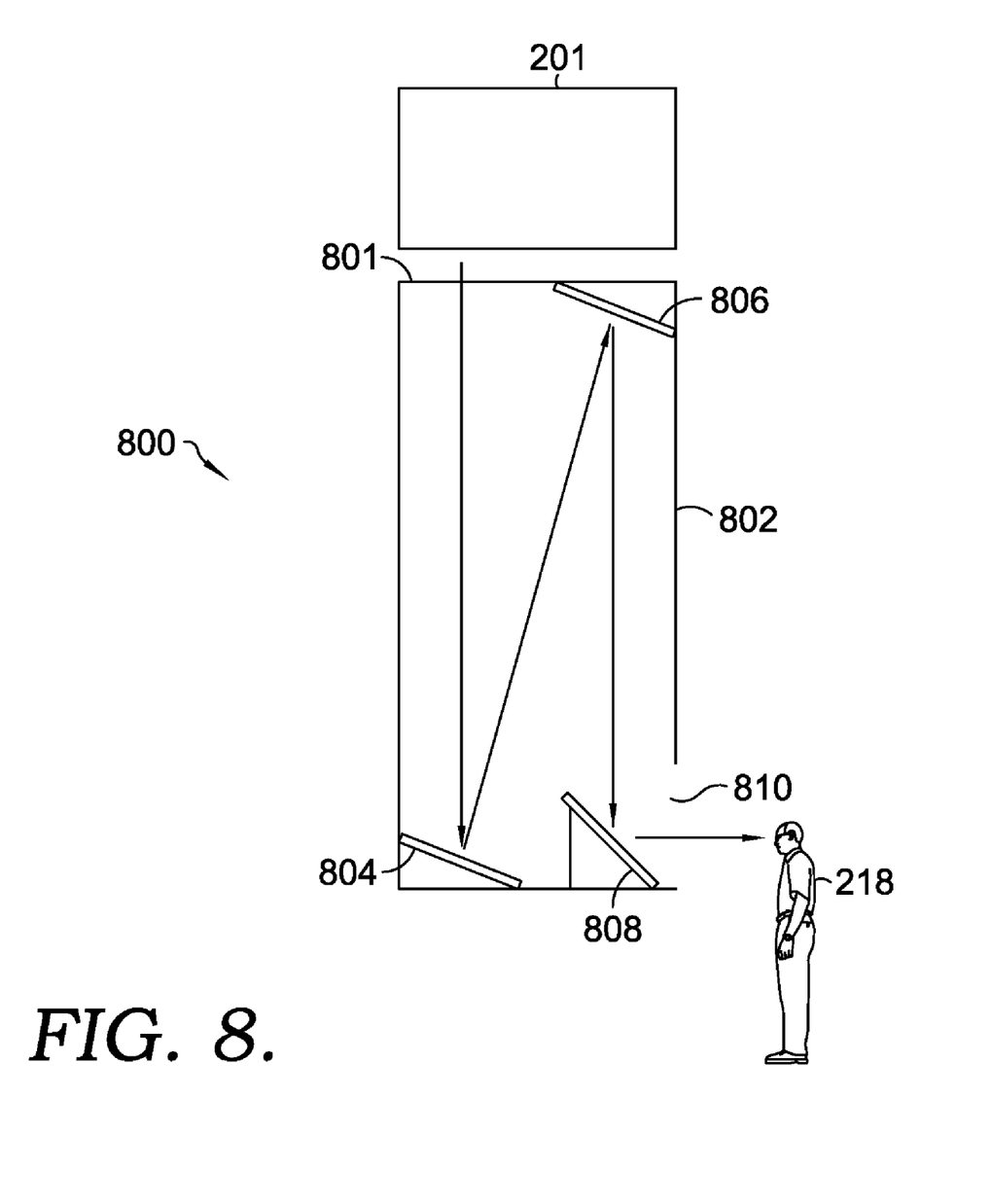
FIG. 8 illustrates a perspective vision tunnel, in accordance with an embodiment of the present invention.

Referring to FIG. 8, a further embodiment of a visual perspective tunnel in accordance with the present invention is illustrated. A display device 801 may output visual indicia into a perspective tunnel 800. Perspective tunnel 800 may comprise a plurality of low reflectance walls 802 which serve to form a tunnel and substantially prevent the intrusion of light from outside the perspective tunnel 800. The plurality of low reflectance walls may be substantially parallel and have an opening 801 at one end to permit entry of visual indicia from display device 801 and an opening 810 to permit egress of the image of a visual indicia from the perspective tunnel 800.

Arranged within the perspective tunnel 800 are a plurality of minors 804, 806 and 808 for reflecting visual indicia within the perspective tunnel 800. While other embodiments of the invention depicted in FIGS. 2-7 depict the openings of the respective perspective tunnels to be at opposite ends of the perspective tunnel, the embodiment depicted in FIG. 8 utilizes an opening 810 in the side of one of the plurality of walls 802 for egress of the visual indicia. A plurality of minors 804, 806 and 808 are utilized to reflect the image of a visual indicia within the perspective tunnel 800 and out opening 810 for viewing by the subject 818. The minors 804, 806, and 808 as illustrated in FIG. 8 are positioned to reflect an image of a visual indicia primarily along the longitudinal axis of the perspective tunnel. A multitude of different configurations of minors may be utilized to reflect the visual indicia within the perspective tunnel 800. The arrangement and proportions of a visual tunnel shown in FIG. 8 is not meant to be limiting in nature.

In FIG. 8 the opening 810 is illustrated as positioned near one end of the perspective tunnel 800. Alternative embodiments of the invention may position the opening 810 at any suitable location along the perspective tunnel 800.

Figure 9:
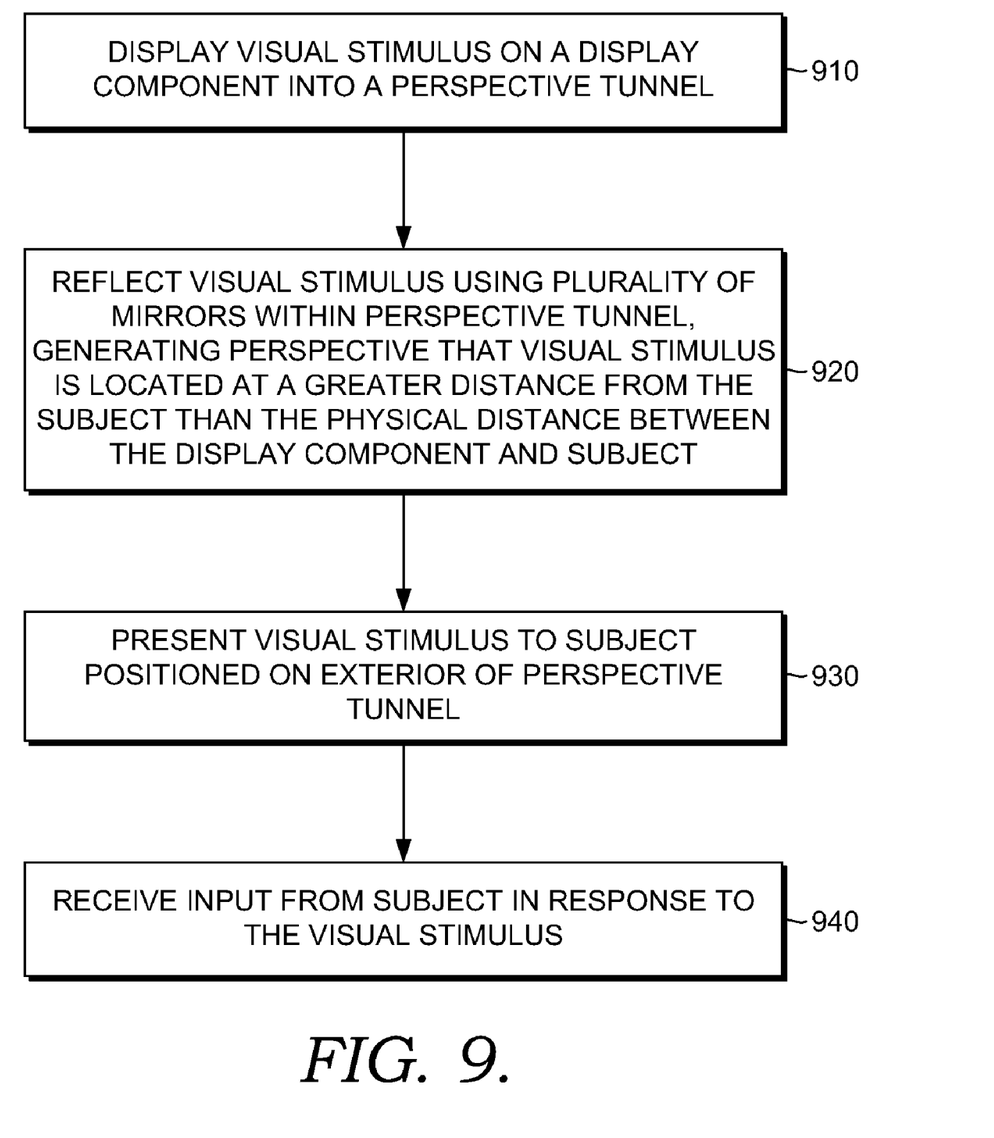
FIG. 9 illustrates a flow diagram showing a method for testing the visual ability of a subject using a perspective vision tunnel, in accordance with an embodiment of the present invention.

Referring to FIG. 9, a flow diagram 900 illustrates a method in accordance with the present invention for testing the visual ability of a subject. Although the terms "step" and "block" are used hereinbelow to connote different elements of methods employed, the terms should not be interpreted as implying any particular order among or between various steps herein disclosed unless and except when the order of individual steps is explicitly described. Initially, in step 910 a visual indicia may be displayed on a display component into a perspective tunnel (e.g., utilizing a display device and perspective tunnel). Any manner of vision test may be administered as part of method 900. The visual stimuli may comprise test images for administering tests that measure a subject's visual ability. Further, a plurality of visual stimuli may be displayed on a display component instead of a single visual stimulus.

At step 920, the image of the visual stimulus is reflected using a plurality of minors within the perspective tunnel. A perspective is generated that the visual stimuli is located at a greater distance from the subject than the physical distance between the subject and the display component. The generated perspective may be substantially equal to optical infinity (e.g., 20 feet or 6 meters).

The visual stimulus is then presented to a subject positioned on the exterior of the perspective tunnel in step 930. The presented visual stimulus may comprise visual indicia for administering a visual ability test as described above.

In response to the visual stimulus, input may be received from the subject in step 940. The subject may provide the appropriate response by interacting with an input device that is connected to the test unit via an input component. Examples of some inputs that may be received from a user and appropriate input devices are discussed in detail in reference to FIG. 1, above.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and is within the scope of the claims.

The invention claimed is:

1. A device for administering a visual acuity test to a subject, the device comprising:
    a display tunnel to output test images;
    a display tunnel defined by a plurality of low reflectance walls, the display tunnel having at least a first portion, the first portion extending substantially perpendicularly to a display; and
    a plurality of minors oriented within the display tunnel to reflect test images output on the display out of the first portion of the display tunnel such that the test images may be visually perceived by the subject,
    wherein the plurality of minors oriented within the display tunnel are arranged to reflect visible light comprising the test images such that the visible light travels a distance greater than the linear distance of the display tunnel by the subject viewing the test images output on the display of the first portion of the display tunnel.

2. The device of claim 1, wherein the test images comprise visual indicia possessing at least one trait.

3. The device of claim 2, wherein the at least one trait possessed by the visual indicia comprises: a directional orientation, a position on the display, one of a predetermined number of mutually exclusive traits, or a combination of traits.

4. The device of claim 1, wherein the display is configured to display a plurality of test images simultaneously.

5. The device of claim 1, wherein the test images are visual indicia for administering visual acuity tests.

6. The device of claim 1, wherein the plurality of mirrors are oriented within the tunnel to reflect test images within the plurality of walls of the tunnel to generate a visual perspective of distance.

7. The device of claim 6, wherein the generated visual perspective of distance is greater than the physical distance between the display and the subject.

8. The device of claim 6, wherein the generated visual perspective of distance is substantially equal to optical infinity.

9. The device of claim 1, wherein the plurality of minors are arranged along the walls of the first portion of the tunnel to reflect the test image within the tunnel to generate a perspective of distance as visually perceived by the subject.

10. The device of claim 9, wherein the generated perspective distance is substantially equal to optical infinity.

11. A device for administering a visual acuity test, the device comprising:
- a perspective tunnel that transmits visible light along the interior of the perspective tunnel, the perspective tunnel comprising a first portion, a second portion, and an output portion, the first portion and the second portion being substantially parallel and the output portion providing egress for visible light from the second portion to the exterior of the perspective tunnel;
- a display to output visual stimuli comprised of visible light into the first portion of the perspective tunnel; and
- a plurality of mirrors oriented within the perspective tunnel such that the visible light comprising the visual stimuli is reflected by the mirrors within the perspective tunnel along the first portion, along the second portion, and then through the output portion to egress the perspective tunnel,
- wherein the plurality of mirrors oriented within the perspective tunnel are arranged to reflect the visible light comprising the visual stimuli such that the visible light travels a distance greater than the linear distance of the perspective tunnel by a test subject viewing the visual stimuli through the output portion of the perspective tunnel.

12. The device of claim 11, wherein the visual stimuli comprise test images for administering visual acuity tests to a test subject.

13. The device of claim 11, wherein the created perspective of distance is substantially equal to optical infinity.

14. The device of claim 11, wherein the plurality of mirrors are arranged along the periphery of the interior of the perspective tunnel.

15. The device of claim 11, wherein the perspective tunnel comprises additional portions being substantially perpendicular to the first and second portions.

16. A method for testing the visual ability of a subject, the method comprising:
- displaying at least one visual stimuli on a display component into a perspective tunnel having a plurality of minors oriented within the perspective tunnel;
- reflecting the at least one visual stimuli using the plurality of mirrors oriented within the perspective tunnel, thereby generating the perspective that the at least one visual stimuli is located at a greater distance from the subject than the physical distance between the display component and the subject;
- presenting the at least one visual stimuli to a subject positioned on the exterior of the perspective tunnel; and
- receiving input from the subject in response to the at least one visual stimuli,
- wherein the plurality of minors oriented within the perspective tunnel are arranged to reflect visible light comprising the visual stimuli such that the visible light travels a distance greater than the linear distance of the perspective tunnel by the subject viewing the visual stimuli through an output portion of the perspective tunnel.

17. The method of claim 16, wherein the at least one visual stimuli comprises at least one visual indicia for administering a visual acuity test to the subject.

18. The method of claim 16, wherein the generated perspective of distance between the location of the at least one visual stimuli and the subject is substantially equal to optical infinity.

* * * * *